United States Patent [19]

Ou et al.

[11] Patent Number: 6,069,288

[45] Date of Patent: May 30, 2000

[54] PROCESS FOR SELECTIVELY SEPARATING HYDROGEN, OR BOTH HYDROGEN AND CARBON MONOXIDE FROM OLEFINIC HYDROCARBONS

[75] Inventors: John D. Y. Ou, Houston; Stephen N. Vaughn, Kingwood; Lawrence G. Daniel, Crosby, all of Tex.

[73] Assignee: Exxon Chemical Patents Inc., Houston, Tex.

[21] Appl. No.: 09/271,948

[22] Filed: Mar. 18, 1999

Related U.S. Application Data

[63] Continuation-in-part of application No. 08/880,611, Jun. 23, 1997, Pat. No. 5,907,067
[60] Provisional application No. 60/033,950, Dec. 31, 1996.
[51] Int. Cl.[7] .................................. C07C 7/00; B01J 8/00; C01B 3/00; C01B 3/12; C01B 3/16
[52] U.S. Cl. .................. 585/800; 585/802; 585/809; 423/247; 423/248; 423/655; 423/656
[58] Field of Search ..................................... 585/800, 802, 585/809; 423/655, 656, 248, 247

[56] References Cited

U.S. PATENT DOCUMENTS

| | | | |
|---|---|---|---|
| 1,911,780 | 5/1933 | White et al. | |
| 3,549,719 | 12/1970 | Duyverman et al. | 260/677 |
| 3,615,217 | 10/1971 | O'Brien et al. | 23/213 |
| 3,855,330 | 12/1974 | Mendelsohn et al. | 260/669 |
| 4,185,039 | 1/1980 | Eden | 260/654 |
| 4,299,800 | 11/1981 | Nishikawa et al. | 423/219 |
| 4,400,364 | 8/1983 | Storm | 423/247 |
| 4,435,607 | 3/1984 | Imai | 585/443 |
| 4,604,275 | 8/1986 | Murib | 423/437 |
| 4,626,521 | 12/1986 | Murib | 502/328 |
| 4,652,687 | 3/1987 | Imai et al. | 585/319 |
| 4,788,371 | 11/1988 | Imai et al. | 585/443 |
| 4,914,075 | 4/1990 | Bricker et al. | 502/330 |
| 5,045,297 | 9/1991 | Bonifaz et al. | 423/437 |
| 5,124,500 | 6/1992 | Clark et al. | 585/655 |
| 5,157,204 | 10/1992 | Brown et al. | 585/850 |
| 5,430,210 | 7/1995 | Grasselli et al. | 585/315 |
| 5,439,859 | 8/1995 | Durante et al. | 502/66 |
| 5,625,116 | 4/1997 | Flammini et al. | 585/848 |

FOREIGN PATENT DOCUMENTS

| | | |
|---|---|---|
| 1231071 | 9/1960 | France . |
| 1 298 985 | 7/1969 | Germany . |
| 690718 | 4/1953 | United Kingdom . |
| 1063420 | 3/1967 | United Kingdom . |
| 1 324 826 | 7/1973 | United Kingdom . |
| WO 95/06018 | 3/1995 | WIPO . |

*Primary Examiner*—Walter D. Griffin
*Assistant Examiner*—Tam M. Nguyen
*Attorney, Agent, or Firm*—Bradley A. Keller

[57] ABSTRACT

A process for the separation and removal, of hydrogen, alone or together with carbon monoxide, if present, from a mixture of these gases with reactive unsaturated hydrocarbons, by contacting the mixture with oxygen over a catalyst at conditions sufficient to oxidize the hydrogen to form water while suppressing reaction of the reactive, unsaturated hydrocarbons. The catalyst contains at least one metal or metal oxide from Groups IB, IIB, IIIB, IVB, VB, VIB, VIIB, and VIII of the Periodic Table, and the temperature of the reaction may range from about 40° C. to about 300° C., the pressure of the reaction ranges from about 14.7 psig to 1,000 psig, and the flow rate of the entering feed ranges from about 1 GHSV to about 50,000 GHSV. Oxygen amounts less than the stoichiometric amount required to react with the hydrogen, and optionally any carbon monoxide, are used. In a second stage, any remaining carbon monoxide is reacted with water in a water gas-shift reaction to give carbon dioxide and hydrogen, and any small remaining hydrogen is reacted with a small portion of reactive unsaturated hydrocarbon present.

22 Claims, No Drawings

6,069,288

PROCESS FOR SELECTIVELY SEPARATING HYDROGEN, OR BOTH HYDROGEN AND CARBON MONOXIDE FROM OLEFINIC HYDROCARBONS

This application claims priority to U.S. Provisional Patent Application Ser. No. 60/033,950, filed Dec. 31, 1996, and is a continuation in part of U.S. patent application Ser. No. 08/880,611, filed Jun. 23, 1997 now U.S. Pat. No. 5,907,067.

FIELD OF THE INVENTION

This invention relates to a process for chemically separating hydrogen, or hydrogen and carbon monoxide, from hydrocarbons containing reactive unsaturates, such as olefins and aromatics. In particular, it relates to a process for the reactive separation of hydrogen and carbon monoxide from olefinic and aromatic hydrocarbons by selective oxidation of the hydrogen and carbon monoxide, with minimal reaction of the olefins and aromatics.

BACKGROUND

The separation of hydrogen and carbon monoxide from mixtures containing reactive unsaturates, such as olefinic and or aromatic hydrocarbons, or mixtures containing light olefinic hydrocarbons such as ethylene, propylene, or other $C_2$–$C_4$ olefins, is a costly, but often necessary, operation because hydrogen and carbon monoxide are contaminants, or poisons for many downstream processes, such as polyethylene and polypropylene manufacturing.

The existing technology for separating hydrogen and carbon monoxide from reactive unsaturated hydrocarbons calls for cryogenic distillation which requires expensive equipment and high energy consumption. Other techniques, such as membrane, and absorption and adsorption are used only for separation of hydrogen from other components, and these techniques are effective only when the system pressure is high; generally greater than 100 psi.

The reason that hydrogen and carbon monoxide are so difficult to separate from mixtures containing light olefins is that the physical properties of the contaminants, hydrogen and carbon monoxide, are very similar to the light olefins in the mixture that they are to be separated from.

For example, carbon monoxide and ethylene, are similar in terms of molecular dimension and bonding characteristics; which makes physical separation very difficult.

Accordingly, there exists a need for an improved process for the selective separation of hydrogen and carbon monoxide from mixtures of these gases with reactive unsaturated hydrocarbons, such as light olefinic hydrocarbons, without significant loss of the valuable olefins via side reactions.

SUMMARY OF THE INVENTION

The invention provides a process for removing hydrogen from a mixture which includes hydrogen and reactive unsaturated hydrocarbons which comprises contacting said mixture with oxygen or an oxygen-containing gas over a catalyst at reaction conditions sufficient to oxidize the hydrogen component of the mixture to form water while suppressing hydrogenation of the reactive unsaturated hydrocarbons of the mixture, and recovering an effluent rich in reactive unsaturated hydrocarbons therefrom.

Another embodiment provides a process for removing hydrogen and carbon monoxide from a mixture which includes hydrogen, carbon monoxide, and reactive unsaturated hydrocarbons which further comprises contacting said mixture, in a second reaction zone with one or more than one catalyst to react remaining carbon monoxide with water (i.e. water gas-shift reaction) and to react residual amounts of hydrogen with reactive unsaturated hydrocarbon.

DETAILED DESCRIPTION

This invention teaches a reactive separation process for separating hydrogen from hydrocarbons containing reactive unsaturated hydrocarbons, including ethylene and propylene. The process involves catalytically reacting hydrogen and oxygen to eliminate the majority of the hydrogen, and then reacting the remaining low-level hydrogen with the reactive unsaturated hydrocarbons. Optionally the reaction product of water and saturated hydrocarbons are removed from the olefinic hydrocarbons. Suitable catalysts can be prepared by distributing metal(s) and/or metal oxide(s) selected from the elements of Groups IB through VIIB and Group VIII on inert supports such as zeolites, clays, alumina, silica, etc. These catalysts can be tailored or arranged in a specific manner to perform selective oxidation of hydrogen and/or controlled hydrogenation of reactive unsaturated hydrocarbons.

The invention further concerns a cost-effective process for separating hydrogen from reactive unsaturated hydrocarbons and other hydrocarbons via staged chemical reactions. In order to completely react out the hydrogen or to reduce the hydrogen level to tens or ones ppm levels, however, one usually would need to add more than the stoichiometric amount of oxygen into the reaction system. This creates a possibility of contamination by the unreacted excess oxygen. The stage-reaction feature of the invention reduces the oxygen contamination problem. The invention involves, in one embodiment, (1) adding slightly less than stoichiometric amounts of oxygen into the reactor and converting all the oxygen and the majority of the hydrogen into water using a catalyst that does not promote any significant amount of reactive unsaturated hydrocarbon hydrogenation, and (2) eliminates essentially all of the remaining hydrogen by hydrogenating the reactive unsaturated hydrocarbons in the stream using a hydrogenation catalyst. By optimizing the extent of reactions (1) and (2), one can remove essentially all of the hydrogen without losing too much of the valuable olefins due to hydrogenation.

The reactive unsaturated hydrocarbons include olefinic compounds such as ethylene, propylene, butylenes, or the like; paraffinic or cyclic compounds such as methane, ethane, propane, butanes, cyclohexane, or the like; and aromatic compounds such as benzene, toluene, xylenes, or the like. The process may be operated in either gas phase or liquid phase. In one of its aspects, a mixture comprised of hydrogen and a light olefinic hydrocarbon, or light olefinic hydrocarbons, is contacted with oxygen or an oxygen-containing gas, e.g., air, over a catalyst highly selective to hydrogen oxidation at reaction conditions sufficient to oxidize the hydrogen component of the mixture to form water, while suppressing reaction of the light olefinic hydrocarbons of the mixture. It is important that the hydrogen-oxidation selective catalyst has no or minimum activity for hydrogenation of reactive unsaturated hydrocarbons. Essentially all of the oxygen is consumed in the reaction zone, with some hydrogen and little if any oxygen passing down stream of the reaction zone.

In another aspect, a mixture comprised of hydrogen, carbon monoxide and a reactive unsaturated hydrocarbon, or a mixture of one or more of such hydrocarbons is contacted in an initial, or first reaction zone of a series, with oxygen or an oxygen-containing gas over a catalyst selective for hydrogen oxidation at conditions sufficient to oxidize the hydrogen component of the mixture to form water, while suppressing hydrogenation of the olefinic components of the mixture to obtain effluent which is fed to a second reaction zone of the series. The catalyst may also be capable of oxidizing carbon monoxide in the presence of oxygen at conditions sufficient to oxidize the carbon monoxide component of the mixture to form carbon dioxide. Alternatively, a different catalyst from that used to oxidize hydrogen may be used to oxidize carbon monoxide. Whether or not the same or different catalysts are used for the two oxidation reactions, the oxidations may either be performed simultaneously together in the first reaction zone, or, in one embodiment, (1) oxidizing the hydrogen component of the mixture to form water in a first portion of said first reaction zone, and subsequently (2) oxidizing the carbon monoxide component of the mixture to form carbon dioxide in a second portion of said first reaction zone. In conducting this series of reactions it is essential to remove the hydrogen first to minimize, avoid, or suppress the hydrogenation reaction between the hydrogen and the reactive unsaturated hydrocarbons.

In the second reaction zone, the effluent is contacted and reacted over an hydrogenation catalyst capable of reacting at least some, and preferably all, of the hydrogen present with a small amount of reactive unsaturated hydrocarbon. The catalyst of the second reaction zone may also be capable of simultaneously reacting the remaining carbon monoxide with water to form carbon dioxide and hydrogen (i.e., the water gas-shift reaction). In one aspect, the function of the second reaction zone is to remove essentially the last traces of the unreacted carbon monoxide from the effluent from the first reaction zone and to remove any newly formed hydrogen (from the water gas-shift reaction) by contacting the effluent with a bifunctional catalyst or two different catalysts for simultaneous water gas-shift reaction and reactive unsaturated hydrocarbon hydrogenation reaction. The concentration of carbon monoxide in the effluent of the first reaction zone, which is fed into the second reaction zone, is preferably controlled and optimized so that (a) there is essentially no oxygen in the effluent of the first reaction zone and (b) the amount of hydrogen generated in the second reaction zone (or the amount of reactive unsaturated hydrocarbon loss due to hydrogenation in the same zone) is acceptably low. An effluent rich in reactive unsaturated hydrocarbons, denuded of oxygen, hydrogen and carbon monoxide, is recovered from this reaction series. The reaction products, which include water and carbon dioxide, can be readily separated from the hydrocarbon product stream using conventional technology, e.g., a drier, amine treatment, caustic washes or the like.

In one embodiment of the invention, (3) reacting remaining carbon monoxide with water to form carbon dioxide and hydrogen (i.e., the water gas-shift reaction) occurs in a first portion of the second reaction zone, while (4) the reaction of at least some, preferably all, of the hydrogen present with the reactive unsaturated hydrocarbon occurs in a second, subsequent portion of the second reaction zone. The same or different catalysts may be used in the first and second portions of the second reaction zone. In an alternate embodiment, both the water gas-shift reaction and the reactive unsaturated hydrocarbon hydrogenation reaction occur simultaneously together in the second reaction zone, using the same or different catalyst for each reaction.

The proposed reactive separation process can either be a one-bed system in which the hydrogen oxidation catalyst and the reactive unsaturated hydrocarbon hydrogenation catalyst are packed in a stacked-bed manner with the oxidation catalyst above the hydrogenation catalyst, or a two-bed-in-series system in which the two catalysts are packed in two separate reactors with the oxidation reactor before the hydrogenation reactor. Oxygen can be introduced into the system at a single point or intermittently at multiple points. However, preferably, the oxygen is introduced only into the first reaction zone or in the hydrogenation/reactive unsaturated hydrocarbon (and optionally, carbon monoxide) mixture prior to introduction of the mixture into the first reaction zone.

The oxidation part of the process must be (i) reactive for hydrogen oxidation, (ii) optionally also reactive for carbon monoxide oxidation, and (iii) inactive for reactive unsaturated hydrocarbon reactions including oligomerization, hydrogenation, oxidation, alkylation, etc. The oxidation part can be accomplished by selecting a suitable catalyst and/or carrying out the oxidation reaction at proper conditions. The catalysts could be prepared by distributing one or more than one active metal or metal oxide on inert supports. The active metals or metal oxides can be selected from Groups IB, IIB, IIIB, IVB, VB, VIB, VIIB, and VIII. Some of the metals in these Groups are reactive for reactive unsaturated hydrocarbon reactions such as hydrogenation. It is possible, however, to eliminate such reactions through the proper, selection of inert supports. The inert supports include zeolites (e.g. the A series, the faujasite series, the ZSM series, the SAPO series, the ALPO series, etc.), clays, alumina, silica, aluminosilicates, other oxides, carbon, etc. The distribution techniques include impregnation, ion exchange, mixing, and chemical deposition. If necessary, the distributed metal(s) could be activated via oxidation and/or reduction.

The temperature of the reaction is generally in the range of from about 408 C to about 3008 C, and is preferably in the range of from about 508 C to about 2508 C. Reactive unsaturated hydrocarbon reactions in the oxidation part can also be minimized by operating the oxidation reaction at low temperatures, typically in the range of less than 75–100° C. The flow rate of the entering feed in the gaseous form is in the range of from about 1 GHSV to about 50,000 GHSV, and is preferably in the range of from about 2000 GHSV to about 10,000 GHSV. The pressure maintained in the reaction zone is generally in the range of from about 14.7 psig to about 1,000 psig, and is preferably in the range of from about 14.7 psig to about 500 psig. Depending on process economics and the objective of contaminant removal, the hydrogen concentration in the effluent can be controlled by adjusting the quantity of oxygen injection. The effluent from this reaction zone could contain several hundred ppm of hydrogen and oxygen to less than 1 ppm hydrogen and oxygen. The latter is preferred.

The hydrogenation part of the process should hydrogenate reactive unsaturated hydrocarbons with the remaining hydrogen in the reaction effluent of the oxidation part. Catalysts for the hydrogenation part could be prepared by distributing one or more than one active metal or metal oxide on inert supports. The active metals or metal oxides can be selected from Groups IB, IIB, IIIB, IVB, VB, VIB, VIIB, and VIII. It is preferred that the inert supports include zeolites (e.g. the A series, the faujasite series, the ZSM series, the SAPO series, the ALPO series, etc.), clays, alumina, silica, aluminosilicates, other oxides, carbon, etc. The distribution techniques include impregnation, ion exchange, mixing, and chemical deposition. If necessary, the distributed metal(s) could be activated via oxidation and/or reduction.

Reactive unsaturated hydrocarbon hydrogenation can usually be maximized by operating the hydrogenation reaction at higher temperatures, typically in the range of higher than 75–100° C. The reaction may be carried out at temperatures in the range of from about 1008 C to about 5008 C, and preferably in the range of from about 1508 C to about 2508 C. Effluent from the first reaction zone is introduced into the second reaction zone at flow rate in the range of from about 1 GHSV to about 50,000 GHSV, and is preferably in the range of from about 2000 GHSV to about 10,000 GHSV. The pressure maintained in the second reaction zone is substantially the same as that maintained in the first reaction zones, generally in the range of from about 14.7 psig to about 1000 psig, and preferably in the range of from about 14.7 psig to about 500 psig. At these conditions, essentially all the resulting hydrogen is consumed by hydrogenation of reactive unsaturated hydrocarbon which takes place in the same reaction zone and produces saturated or paraffinic hydrocarbons. Optionally, any remaining carbon monoxide may be simultaneously reacted with water to form carbon dioxide and hydrogen (i.e. the water gas-shift reaction). The same catalysts suitable for the hydrogenation reaction will be suitable for the water gas-shift reaction or, optionally, a different catalyst can be used for the water gas-shift reaction. As noted, hydrogen produced in the water gas-shift reaction will be consumed in the reactive unsaturated hydrocarbon hydrogenation reaction. In this way, hydrogen and carbon monoxide can be essentially completely purged from the system with minimal loss of the reactive unsaturated hydrocarbon product. Since the quantity of carbon monoxide fed to the second reaction zone is controlled at acceptably low levels, the quantity of hydrogen generated and consequently the amount of ethylene loss via hydrogenation would not be sufficient to jeopardize the economics.

In conducting the two-reaction-zone process for the purpose of producing an olefinic stream that is completely denuded of oxygen, hydrogen, and carbon monoxide via hydrogen and carbon monoxide oxidation reactions, oxygen is introduced into the reaction zones in concentration less than that required to react stoichiometrically with the hydrogen and, optionally, carbon monoxide present in the first reaction zone. In other embodiments, the amount of oxygen introduced is in the range of from about 1 mole % to less than about 100 mole %, preferably from about 50 mole % to less than about 100 mole %, most preferably in the range of from about 90 mole % to about 99 mole %, based on the amount of oxygen required to react stoichiometrically with the hydrogen and, optionally, carbon monoxide present in the first reaction zone. At these reaction conditions, this amount of oxygen reacts with substantially all of hydrogen and most of carbon monoxide, while simultaneously avoiding or suppressing hydrogenation and oxidation of the reactive unsaturate. The amount of oxygen in the effluent from the first reaction zone generally does not exceed about 100 wppm, and preferably does not exceed about 1 wppm, and most preferably is not present. The total of the oxygen or oxygen-containing gas required for these reactions can be introduced into or prior to the first reaction zone. Since no oxygen is needed in the second reaction zone, no oxygen should be supplied directly to the second reaction zone. Oxygen can be supplied via one or a plurality of oxygen injection points located within the first reaction zone. The effluent from the first reaction zone will contain essentially no hydrogen or a controlled amount of hydrogen and unreacted carbon monoxide. In one non-limiting embodiment of the invention, the amount of hydrogen is less than that in the initial mixture. The conditions of operation in each of the reaction zones is thus sufficient to reduce the concentration of hydrogen to levels below about 500 ppm, preferably below 100 wppm, most preferably below about 1 wppm; and the concentration of carbon monoxide to levels below 100 ppm by volume, and preferably below 1 ppm by volume. Minimal amounts of the reactive unsaturated hydrocarbons are hydrogenated in the zones, loss of reactive unsaturated hydrocarbons within these zones generally not exceeding about 1% by volume based on the olefins in the feed to the first reaction zone; and preferably does not exceed about 0.1% by volume. Thus, generally at least about 95.0 volume %, or from about 95.0 volume % to about 99.9 volume %, preferably from about 99.5 volume % to about 99.9 volume % of the reactive unsaturated hydrocarbons in the feed to the first reaction zone are recovered. It is not necessary to remove the oxidation products of hydrogen and carbon monoxide, e.g., water and carbon dioxide, from the effluent of the first reaction zone. If desirable, the reaction products can be readily separated from the reactive unsaturated hydrocarbon product stream after the second reaction zone using conventional technology, e.g., a drier, amine treatment, caustic washes or the like.

Catalysts suitable for the first reaction zone constitute of a composite inclusive of one or more than one of the metals or metal oxides selected from Groups IB, IIB, IIIB, IVB, VB, VIB, VIIB, and VIII with the metal silver being preferred and inert porous supports, if desired, include zeolites, carbon, inorganic oxides and mixed oxides including silica, alumina, physically or chemically modified alumina, physically or physically modified silica, aluminosilicate, magnesium oxide, clay, zirconia, titania, porous glass, etc. A preferred catalyst is a bulk silver catalyst or silver composed with an inorganic oxide support. The metals or metal oxides are chosen for their low activity or inactive nature for reactions of the reactive unsaturates including particularly hydrogenation, as well as oligomerization, oxidation, alkylation, or other chemical reaction at the conditions of operation. The metal(s), and/or metal oxide(s), may be placed on the porous support using techniques such as impregnation, ion exchange, vapor deposition, mixing, dispersion, or the like. The concentration of the metal(s) and/or metal oxide(s) is generally in the range from about 0.01 wt. % to about 75 wt. %, and is preferably in the range of from about 0.2 wt. % to about 5 wt. %, based on the weight of total catalyst (dry basis).

Catalysts suitable for the second reaction zone constitute of a composite inclusive of one or more than one of the metals or metal oxides selected from Groups IB, IIB, IIIB, IVB, VB, VIB, VIIB, and VIII and the elements of copper and zinc, and inert porous supports include zeolites, carbon, inorganic oxides and mixed oxides including silica, alumina, physically or chemically modified alumina, physically or physically modified silica, aluminosilicate, magnesium oxide, clay, zirconia, titania, porous glass, etc. The metals or metal oxides are chosen for their low activity or inactive nature for olefin reactions including oligomerization, oxidation, alkylation, or other chemical reaction at the conditions of operation. The metal(s), and/or metal oxide(s), may be placed on the porous support using techniques such as impregnation, ion exchange, vapor deposition, mixing, dispersion, or the like. The concentration of the metal(s) and/or metal oxide(s) is generally in the range of from about 0.01 wt. % to about 100 wt. %, and is preferably in the range of from about 1.0 wt. % to about 50 wt. %, based on the weight of total catalyst (dry basis).

The process of this invention could include a stacked-bed reactor with both catalysts operating at similar temperature ranges or with two reactors in series in which the first oxidation reactor at a temperature at lower than 100° C. and the second hydrogenation reactor at higher than 75° C. As noted, the first and second reaction zones may be independently separated into first and second sequential portions.

The following examples are illustrative of the more salient features of the invention. The separation performance can be improved through catalyst and process optimization. All temperatures are given in terms of degrees Centigrade, and parts and percentages are given in terms of weight except as otherwise specified.

EXAMPLE 1

This Example illustrates the carbon monoxide-selective oxidation system induced by a platinum catalyst. The Powerforming catalyst manufactured by the Criteria Company of Houston with a 0.6 wt. % platinum-on-alumina catalyst was selected. It was loaded into a ½" (1.27 cm) OD×1¾" (4.44 cm) long stainless steel reactor and reduced under hydrogen at 3508 C prior to use. The feed stream was a mixture of 420 ppm oxygen, 962 wppm carbon monoxide, 20 ppm $CO_2$, 5.7 vol. % hydrogen, 77.2 vol. % ethylene, 17.1 vol. % propylene, 0.4 vol. % butene-1, 140 ppm methane, 140 ppm ethane, and 350 ppm propane. The feed was passed over the catalyst and reacted at the conditions of 738 C, 24 psig, and a flow rate of approximately 5000 GHSV (gas hourly space velocity). Olefin hydrogenation was monitored by measuring the concentration of ethane in the feed and the product using GC. CO and $CO_2$ concentrations in the feed and the product were used to measure CO oxidation. $H_2$ oxidation was monitored by measuring the water content in the feed and the product. Oxygen concentration was analyzed using an oxygen analyzer manufactured by Teledyne Analytical Instruments, Inc.

Results are listed below:

TABLE 1

|  | $O_2$, wppm | CO, wppm | $CO_2$, wppm | $H_2O$, wppm | Ethane, wppm |
| --- | --- | --- | --- | --- | --- |
| Feed | 420 | 962 | 20 | <1 | 140 |
| Product | 200 | 410 | 530 | 20 | 630 |

The test indicates Pt-based catalysts' oxidation selectivity toward CO over $H_2$ and ethylene. Furthermore, the ethylene hydrogenation was maintained at a fairly low level of about 500 ppm. Thus, CO can be selectively removed via oxidation to form $CO_2$. The separation performance can be readily further improved through catalyst and process optimization.

EXAMPLE 2

This Example illustrates the selective removal of hydrogen from ethylene using a silver catalyst. The catalyst (TOR-20X, by Enichem Co., Japan) contained 2 wt. % Ag on alumina. The feed stream was a mixture of 56 wppm oxygen, 1040 wppm carbon monoxide, 5.0 vol. % hydrogen and 94.9 vol. % ethylene. The catalyst was employed without reduction. The reaction was conducted at 808 C, 325 psig, and 5000 GHSV. No ethane formation (i.e. ethylene hydrogenation) was detected. The main reaction was $H_2$ and oxygen to form water (see Table 2), which would be useful for selectively removing $H_2$ from ethylene. The composition of the feed and products of the reaction are summarized in Table 2.

TABLE 2

|  | $O_2$, wppm | CO, wppm | $CO_2$, wppm | $H_2O$, wppm | Ethane, wppm |
| --- | --- | --- | --- | --- | --- |
| Feed | 56 | 1040 | 5 | 5 | 130 |
| Product | <1 | 1035 | 9 | 120 | 130 |

Essentially no ethylene was hydrogenated during the reaction; no ethane formation having been detected.

EXAMPLE 3

This Example illustrates the selective removal of hydrogen and carbon monoxide from an olefin stream by oxidation of both the hydrogen and carbon monoxide using a staged reactor system. Three reactors were employed in series: a first reactor which contained the same silver catalyst as in Example 1, except that the catalyst was reduced under hydrogen at 2508 C for 16 hours prior to use; a second reactor which contained a catalyst constituted of 2.8 wt. % platinum on a 3A molecular sieve, prereduced at 3508 C for 3 hours prior to use; and a third reactor which contained a commercial low temperature shift gas catalyst (Katalco 53-1, ⅓ CuO+⅓ ZnO+⅓ $Al_2O_3$) which had been prereduced at 2208 C under hydrogen for a 24 hour period.

A feed was prepared by mixing a hydrocarbon stream of 94.342% ethylene, 5.294% $H_2$, 0.342% CO, and 0.022% ethane with an oxygen-containing stream (90% nitrogen+10% oxygen). After the mixing, the feed had a composition of 71.455% ethylene, 22.137% nitrogen, 4.010% $H_2$, 2.123% $)_2$, 0.259% CO, and 0.017% ethane.

The feed was introduced into the first reactor with the effluent from the first reactor flowing as feed to the second reactor of the series, and the effluent from the second reactor flowing as feed to the third reactor of the series. The first reactor was operated at 1768 C, 20 psig, and 2000 GHSV, conditions under which hydrogen was selectively oxidized to water. The second reactor was operated at 1048 C, 20 psig, and 2000 GHSV, conditions at which carbon monoxide was oxidized to carbon dioxide. In the third reactor, which was operated at 2018 C, 20 psig, and 2000 GHSV, residual carbon monoxide was reacted with water to carbon dioxide and hydrogen. The resulting hydrogen was eliminated in situ via a secondary hydrogenation reaction with ethylene. These results are summarized in Table 3.

TABLE 3

|  | Feed | Effluent Feed from First Reactor | Effluent Feed from Second Reactor | Effluent Feed from Third Reactor |
| --- | --- | --- | --- | --- |
| Ethylene, Volume % | 71.455 | 76.848 | 77.405 | 77.265 |
| $N_2$, Volume % | 22.137 | 22.795 | 22.250 | 22.359 |
| $H_2$, Volume % | 4.010 | 0.029 | 0.029 | 4 ppm |
| $O_2$, Volume % | 2.123 | 0.065[1] | 25 ppm[1] | 1 ppm[1] |
| CO, Volume % | 0.259 | 0.246 | 0.116 | 80 ppm |
| Ethane, Volume % | 0.017 | 0.029 | 0.045 | 0.102 |
| $CO_2$, Volume % | NA | 0.053 | 0.154 | 0.266 |

As illustrated by these examples, one can see how the hydrogen and oxygen levels across the first reactor are reduced without the undesirable effect of hydrogenating the ethylene.

In the second reactor, the level of carbon monoxide is reduced and the residual oxygen is consumed. In the third reactor, the level of oxygen is even further reduced.

EXAMPLE 4

In this Example, hydrogen is removed from a mixture of hydrogen and ethylene by selective oxidation of the hydrogen over a silver catalyst, without significant hydrogenation of the ethylene. A gaseous feed constituted of a mixture of 92.02 mol % ethylene, 5.81 mol % hydrogen, 2.13 mol % oxygen, 0.02 mol % ethane, 0.01 mol % carbon monoxide, 0.0005 mol % carbon dioxide, and 0.0005 mol % water, was reacted over a 2 wt. % Ag-on-alumina catalyst (TOR-20X, from Enichem Co., Japan) at 150° C., 20 psig, and 2000 GHSV. The $O_2/H_2$ molar ratio was 0.37, significantly lower than stoichiometric. The catalyst was reduced under hydrogen at 250° C. for 16 hours prior to use. The composition of the feed and gaseous products of the reaction are summarized in Table 4, below. Note that (1) all compositions are in mol %, (2) product composition excludes liquid water, (3) the value for gaseous water is that of saturation, and (4) ND means non-detected.

TABLE 4

| | $C_2H_4$ | $H_2$ | $O_2$ | $C_2H_6$ | CO | $CH_4$ | $CO_2$ | $H_2O$ |
|---|---|---|---|---|---|---|---|---|
| Feed | 92.02 | 5.81 | 2.13 | 0.02 | 0.01 | ND | 0.0005 | 0.0005 |
| Prod. | 97.28 | 2.22 | 0.01 | 0.11 | 0.0001 | ND | 0.01 | 0.37 |

These data thus show that the principal Ag catalyst reaction was between hydrogen and oxygen to form water. Significant hydrogen remains in the product due to the lower than stoichiometric concentration of oxygen. Essentially no ethylene was hydrogenated during the reaction; little ethane formation having been detected. Note also the reduction of carbon monoxide and the increase of carbon dioxide, indicating some oxidation of the carbon monoxide to carbon dioxide.

EXAMPLE 5

This Example illustrates the selective removal of hydrogen from an olefin stream using a staged oxidation-hydrogenation reactor system. Two reactors were employed in series: the first reactor was the same one described in Example 4; the second reactor contained a 0.6 wt. % platinum-on-alumina catalyst (PHF-4, from Criterion Catalyst Co., USA) and was operated at 50° C., 20 psig, and 2000 GHSV. The Pt catalyst was reduced under hydrogen at 350° C. for 16 hours prior to use. Feed was introduced into the first reactor with the effluent from the first reactor flowing to the second reactor of the series.

The initial gaseous feed was the same one described in Example 4. The composition of initial feed and gaseous products of the two reactions are summarized in Table 5a, below. Note that (1) all compositions are in mol %, (2) product composition excludes liquid water, (3) the value for gaseous water is that of saturation, and (4) ND means non-detected.

TABLE 5a

| | $C_2H_4$ | $H_2$ | $O_2$ | $C_2H_6$ | CO | $CH_4$ | $CO_2$ | $H_2O$ |
|---|---|---|---|---|---|---|---|---|
| Feed | 92.02 | 5.81 | 2.13 | 0.02 | 0.01 | ND | 0.0005 | 0.0005 |
| 1 Prod. | 97.28 | 2.22 | 0.01 | 0.11 | 0.0001 | ND | 0.01 | 0.37 |
| 2 Prod. | 98.08 | 0.02 | 0.01 | 1.50 | ND | 0.0001 | 0.02 | 0.37 |

These data thus show that the principal reaction of the Pt catalyst was between hydrogen remaining from reactor 1 and ethylene to form ethane. Ethylene was hydrogenated during the second stage reaction; significant ethane formation having been detected.

To optimize performance by minimizing ethylene hydrogenation, the oxygen concentration in the feed was increased to a near stoichiometric molar ratio of 0.49 $O_2/H_2$. The new composition of feed and gaseous product from reactor 2 are summarized in Table 5b below.

TABLE 5b

| | $C_2H_4$ | $H_2$ | $O_2$ | $C_2H_6$ | CO | $CH_4$ | $CO_2$ | $H_2O$ |
|---|---|---|---|---|---|---|---|---|
| Feed | 90.60 | 6.30 | 3.07 | 0.03 | 0.01 | ND | 0.0005 | 0.0005 |
| 2 Prod. | 99.36 | 0.02 | 0.07 | 0.10 | ND | 0.0004 | 0.06 | 0.40 |

These data thus show that the principal reaction was between hydrogen and oxygen to form water over the Ag catalyst in the first reactor. Little hydrogen remains in the first stage product, due to the near stoichiometric concentration of oxygen in the feed. As a result, the reaction of hydrogen and ethylene to form ethane over the Pt catalyst in the second stage reactor is minimal; little ethane formation having been detected.

One can see the benefits of this invention enable one to selectively separate hydrogen and carbon monoxide from a reactive unsaturate without significant loss of the reactive unsaturate via undesirable side reactions.

We claim:

1. A process for removing hydrogen from a mixture which includes hydrogen, and unsaturated hydrocarbons which comprises
   (a) contacting said mixture in a first reaction zone, in the presence of oxygen or an oxygen-containing gas in such an amount that the amount of oxygen present is less than the stoichiometric amount of oxygen required to react with the hydrogen over a catalyst comprising one or more than one of the metals or metal oxides selected from the elements of Groups IB, IIB, IIIB, IVB, VB, VIB, VIIB, and VIII of the Periodic Table of Elements at reaction conditions sufficient to oxidize the hydrogen component of the mixture to form water while suppressing hydrogenation of the unsaturated hydrocarbons of the mixture, and removing therefrom an effluent which contains less hydrogen than was present in the mixture,
   (b) contacting said effluent, in a second reaction zone, over a catalyst at conditions sufficient to react at least some of the hydrogen present with unsaturated hydrocarbon,
   (c) recovering from said second reaction zone an effluent rich in unsaturated hydrocarbons and denuded of hydrogen.

2. The process of claim 1 wherein in said first reaction zone the temperature of the reaction ranges from about 408 C to about 3008 C and the flow rate of the entering feed ranges from about 1 GHSV to about 50,000 GHSV, and in said second reaction zone the temperature of the reaction ranges from about 40° C to about 300° C, and the flow rate that the effluent is introduced into said second reaction zone ranges from about 1 GHSV to about 20,000 GHSV.

3. The process of claim 1 wherein in said first reaction zone the temperature of the reaction ranges from about 50° C to about 250° C and the flow rate of the entering feed ranges from about 2000 GHSV to about 10,000 GHSV, and in said second reaction zone the temperature of the reaction ranges from about 50° C to about 200° C and the flow rate of the entering feed ranges from about 2000 GHSV to about 10,000 GHSV.

4. The process of claim 1 wherein the catalyst of said first reaction zone comprises silver.

5. The process of claim 1 wherein the catalyst of said first reaction zone comprises an inert porous support selected from carbon, inorganic oxides, and mixtures thereof.

6. The process of claim 1 wherein the catalyst of said first reaction zone comprises a zeolite.

7. The process of claim 1 wherein the catalyst of said second reaction zone comprises one or more than one of the metals and/or metal oxides selected from the elements of Groups IB, IIB, IIIB, IVB, VB, VIB, VIIB, and VIII of the Periodic Table of Elements.

8. The process of claim 1 wherein the catalyst of said second reaction zone comprises an inert porous support selected from carbon, inorganic oxides, and mixtures thereof.

9. The process of claim 1 wherein the catalyst of said second reaction zone is a Group VIII noble metal.

10. A process for removing hydrogen and carbon monoxide from a mixture which includes hydrogen, carbon monoxide, and unsaturated hydrocarbons which comprises (a) contacting said mixture in a first reaction zone, in the presence of oxygen or an oxygen-containing gas in such an amount that the amount of oxygen present is less than the stoichiometric amount of oxygen required to react with the hydrogen and carbon monoxide over a catalyst comprising one or more than one of the metals or metal oxides selected from the elements of Groups IB, IIB, IIIB, IVB, VB, VIB, VIIB, and VIII of the Periodic Table of Elements at reaction conditions sufficient to
(1) oxidize the hydrogen component of the mixture to form water, and
(2) oxidize the carbon monoxide component of the mixture to form carbon dioxide
while suppressing hydrogenation of the unsaturated hydrocarbons of the mixture, and removing therefrom an effluent which contains less hydrogen than was present in the mixture, (b) contacting said effluent, in a second reaction zone, over at least one catalyst at conditions sufficient to
(3) react remaining carbon monoxide with water to form carbon dioxide and hydrogen, and
(4) react at least some of the hydrogen present with unsaturated hydrocarbon, (c) recovering from said second reaction zone an effluent rich in unsaturated hydrocarbons and denuded of hydrogen and carbon monoxide.

11. The process of claim 10 wherein in said first reaction zone the temperature of the reaction ranges from about 40° C to about 300° C and the flow rate of the entering feed ranges from about 1 GHSV to about 50,000 GHSV, and in said second reaction zone the temperature of the reaction ranges from about 40° C to about 300° C, and the flow rate that the effluent is introduced into said second reaction zone ranges from about 1 GHSV to about 20,000 GHSV.

12. The process of claim 10 wherein in said first reaction zone the temperature of the reaction ranges from about 50° C to about 250° C and the flow rate of the entering feed ranges from about 2000 GHSV to about 10,000 GHSV, and in said second reaction zone the temperature of the reaction ranges from about 50° C to about 200° C and the flow rate of the entering feed ranges from about 2000 GHSV to about 10,000 GHSV.

13. The process of claim 10 wherein the catalyst of said first reaction zone comprises silver.

14. The process of claim 10 wherein the catalyst of said first reaction zone comprises an inert porous support selected from carbon, inorganic oxides, and mixtures thereof.

15. The process of claim 14 wherein the catalyst of said first reaction zone comprises a zeolite.

16. The process of claim 10 wherein the catalyst of said second reaction zone comprises one or more than one of the metals and/or metal oxides selected from the elements of Groups IB, IIB, IIIB, IVB, VB, VIB, VIIB, and VIII of the Periodic Table of Elements.

17. The process of claim 10 wherein the catalyst of said second reaction zone comprises an inert porous support selected from carbon, inorganic oxides, and mixtures thereof.

18. The process of claim 10 wherein the catalyst of said second reaction zone is a Group VIII noble metal.

19. The process of claim 10 where
(1) oxidizing the hydrogen component of the mixture to form water occurs in a first portion of said first reaction zone, and
(2) oxidizing the carbon monoxide component of the mixture to form carbon dioxide occurs in a second portion of said first reaction zone.

20. The process of claim 10 where
(3) reacting remaining carbon monoxide with water to form carbon dioxide and hydrogen occurs in a first portion of said second reaction zone, and
(4) reacting at least some of the hydrogen present with unsaturated hydrocarbon occurs in a second portion of said second reaction zone.

21. The process of claim 10 where
(1) oxidizing the hydrogen component of the mixture to form water, and
(2) oxidizing the carbon monoxide component of the mixture to form carbon dioxide
both occur simultaneously together in said first reaction zone.

22. The process of claim 10 where
(3) reacting remaining carbon monoxide with water to form carbon dioxide and hydrogen, and
(4) reacting at least some of the hydrogen present with unsaturated hydrocarbon
both occur simultaneously together in said second reaction zone.

* * * * *